United States Patent [19]

Frampton

[11] 3,969,274

[45] July 13, 1976

[54] FIXED BED CATALYST

[75] Inventor: Orville D. Frampton, Wyoming, Ohio

[73] Assignee: National Distillers and Chemical Corporation, New York, N.Y.

[22] Filed: Mar. 14, 1974

[21] Appl. No.: 451,259

[52] U.S. Cl. .............................. 252/456; 252/457; 252/458; 252/459; 252/460
[51] Int. Cl.² ................... B01J 29/16; B01J 29/26; B01J 29/00; B01J 29/10
[58] Field of Search ........... 252/456, 457, 458, 459, 252/460

[56] References Cited
UNITED STATES PATENTS

| | | |
|---|---|---|
| 3,014,899 | 12/1961 | Engel .............................. 252/456 X |
| 3,243,385 | 3/1966 | Sennewald et al. .............. 252/456 X |
| 3,414,606 | 12/1968 | Winderl et al. ................. 252/456 X |
| 3,493,517 | 2/1970 | Jaffe .............................. 252/458 X |

*Primary Examiner*—Paul F. Shaver
*Attorney, Agent, or Firm*—Kenneth D. Tremain

[57] ABSTRACT

An improved fixed bed catalyst is disclosed and comprises the active catalyst material supported on a particular type of porous silica xerogel which has been treated with steam under particular temperature conditions.

18 Claims, No Drawings

FIXED BED CATALYST

BACKGROUND OF THE INVENTION

The use of silica gel as a support for catalysts is well known. The silica gel is a colloidal system of solid character comprised of colloidal particles of a condensation polymerized silicic acid in a hydrated state which forms a coherent structure. It is an assembly of small, impervious, dense, roughly spherical (diameter roughly 100 A) particles in a rather open or loose random packing. The particles are believed to be spherical since the gels are not crystalline. It is believed that the spheres are bonded together by bridges or fillets of the same material. The pore system within the aggregate is formed by the open spaces between the elementary particles and the porous texture, as characterized by the specific surface area, pore volume and pore diameter, depends on the size and the packing of the elementary particles. There are generally two forms of silica gel — xerogel and aerogel.

An aerogel is a gel in which the liquid phase of a gelled silicic acid solution has been replaced by a gaseous phase in such a way as to avoid the shrinkage which would occur if the gel had been dried directly from a liquid. For example, Kistler prepared silica aerogels by replacing most of the water in the gel with alcohol, heating the gel in an autoclave above the critical temperature of the alcohol so that there was no meniscus between the liquid and gas phases, and venting the vapors. In this way, liquid phase was removed without subjecting the gel structure to the compressive forces due to the surface tension of the liquid-gas interface.

Xerogels are prepared by removal of the water by evaporation from an aqueous gelled silicic acid solution. Evaporation of the liquid phase forms menisci in the pores at the surface of the gel so that the surface tension of the liquid exerts a strong compression on the gel mass. The degree to which the gel can be densified depends on the equilibrium between the compression due to the surface tension and the resistance to compression by the gel framework. Compression will increase with smaller pore diameters; resistance to compression depends upon the strength of the gel which increases with higher packing density and more strongly coalesced structures. Thus, gels of high specific surface, made up of extremely small ultimate silica units and formed at low silica concentration, shrink greatly and crack into fragments upon being dried.

Much of the technology of silica gels involves the problem of making a strong hard gel mass which will not shrink or crack upon being dried and which will be suitable as a catalyst base. On the other hand, there has evolved a considerable art in producing extremely light, friable gels which will break down easily into fine powders for use as fillers in plastics, rubber and the like. This type of xerogel is not suitable for fixed bed catalyst supports.

Other solid forms of silica include the crystalline quartz, tridymite and cristobolite, and these are generally not suitable as catalyst supports because, in part, they are non-porous. The same is true of opal, an amorphous form of silica.

Pelleted diatomaceous earth is a naturally occurring form of siliceous material which is sometimes used as a catalyst support because it has a porous structure and is relatively crush-resistant. However, it also contains alumina and iron impurities which may be harmful to many catalytic reactions.

There is a significant amount of technical literature relating to combining a type of hydrothermal treatment of silica gel with its use as a catalyst. For example, Czarny et al, Przem. Chem. 46 (4), 203-207 (1967), studied the effect of water pressure (a hydrothermal treatment) and suggested the use of these gels to study the influence of pore structure on catalytic properties. German Offen. 2,127,649 teaches preparing macroporous silica gel spheres by heating them in steam and aqueous ammonia for 3 hours at 10 bars and the resulting material is reported to be useful for catalytic processes. French Pat. No. 1,585,305, refers to a method for hardening the surfaces of silica gel without degrading its activity or altering its properties using a heat treatment in a lower alcohol vapor with 10% of its volume as water. Schlaffer et al, J.Phys.Chem. 69 (5), 1530-6 (1965), examined the physical changes that occur to silica and alumina gels upon exposure to steam at moderate to high temperatures and found the surface area and pore volume of silica gel to be less stable to prolonged steaming those those of silica-alumina cracking catalysts.

Other technical literature relates to increasing the crushing strength of silica gel by a steam or water treatment. See, e.g., Bodnikov et al, Zh.Prikl.Khim. 38 (10), 2157–65 (1965) and Sultanov, U.S.S.R. Pat. No. 281,431. A number of other papers deal with the steam treatment of silica gel to alter pore characteristics.

German Offen. 2,237,015 relates to a phosphoric acid hydration catalyst supported on a treated silica gel carrier. The silica gel carrier material is treated with steam or a mixture of steam and nitrogen at a temperature of 200°–350° C., preferably 250°–300° C., and a pressure of 30-1500 psig to obtain a material of increased crushing strength.

Although the German Offen. teaches that the steam treatment of silica gel will increase its crushing strength, it is important to note that the crush strength of the gel is not, per se, transferrable to the phosphoric acid impregnated catalyst. For example, a sample of virgin grade 57 ID silica xerogel has an average crush strength of 4.7 pounds with 14% equal to or less than 2 pounds while a phosphoric acid olefin hydration catalyst made from that xerogel has a much lower average crush strength of 2 pounds with 72% ≤ 2 pounds.

I have now found that by steam treating certain silica xerogels, a xerogel of improved crush strength can be obtained which can be used as a support for various catalytic materials and the resulting catalyst will have an improved crush strength and certain other surprising and unexpected advantages which are described in more detail below.

Accordingly, it is the object of this invention to provide a fixed bed supported catalyst having properties superior to that obtained in the prior art. This and other objects of the invention will become apparent to those skilled in the art from the following detailed description.

SUMMARY OF THE INVENTION

This invention relates to a fixed bed supported catalyst and more particularly to a fixed bed supported catalyst in which the support is a silica xerogel which has been treated with steam under certain specific temperature conditions.

DESCRIPTION OF THE PREFERRED EMBODIMENTS

In accordance with the preferred embodiments of the present invention, a silica xerogel of improved crush resistance is first prepared and is then impregnated with the active catalytic material. As noted above, xerogels can be produced as strong, hard masses or as extremely light, friable gels. Only the former is suitable for the catalyst of this invention.

Accordingly, the silica gel used to prepare the catalyst of this invention must be either a regular density (RD) or intermediate density (ID) silica xerogel or ID extrudates which are characterized by the following properties:

| | | |
|---|---|---|
| Martin diameter: | 0.5–25.0 mm, preferably 2.0–5.0 mm | |
| Bulk density: | 0.35–0.75 g/cc, preferably 0.42–0.70 g/cc | |
| Pore volume: | 0.40–2.2 ml/g, preferably 0.44–1.15 ml/g | |
| BET surface area: | 200–900 m$^2$/g | |
| Chemical composition: | $SiO_2$ | >99w% (dry basis) |
| | $Fe_2O_3$ | 0.01–0.03 w% (dry basis) |
| | $Na_2O$ | 0.02–0.09 w% (dry basis) |
| | $Al_2O_3$ | 0.4 w% (dry basis) |
| Average crush strength (dry) of 50 particles: | >2.0 pounds | |

The average crush strength of the xerogel is determined with a Chatillon Pellet Strength tester which measures the minimum force necessary to just crush a particle between parallel plates.

Intermediate density xerogels have a bulk density of 0.35–0.48 g/cc, pore volume of 0.80–2.2 ml/g and BET surface area of 200–500 m$^2$/g; regular density xerogels have a bulk density of 0.65–0.75 g/cc, pore volume of 0.3–0.5 ml/g and BET surface area of 600–900 m$^2$/g. Suitable xerogels are commercially available. Examples of intermediate density materials include grade 57 intermediate density (ID) silica gel manufactured by Davison Chemical Co., Division of W. R. Grace & Co., Baltimore, Md. and 3–12 mesh ID silica gel manufactured by Eagle Chemical Co., Mobile, Alabama. Examples of regular density (RD) xerogels include grade 03 regular density gel manufactured by the Davison Chemical Co.

The silica xerogel particle is placed into a reactor which is then sealed from the atmosphere and purged of air with an inert gas such as nitrogen or the like. The xerogel is exposed to water vapor as it is heated under pressure until the treatment temperature is reached at both the inlet and outlet zones of the reactor. Heating can be accomplished by heating the reactor or by passing a hot flowing inert gas, optionally saturated with water vapor through the reactor. It is important, however, that no liquid water be present.

Once the appropriate temperature and pressure conditions are attained, the gel is steamed for a period of time which can range from 4–16 hours. The water vapor can be used by itself or can optionally be diluted with an inert gas such as nitrogen or ethylene. Total pressure employed will be in the range of 40 psi to 1500 psi and the water vapor will contribute a partial pressure in the range of 40–225 psi. The treatment temperature is at least 149° C. and care is taken not to allow the temperature to attain a level above 300° C. When the xerogel is heated to the treating temperature from ambient temperature, the vapor above the xerogel preferably should be saturated with water up to at least 149° C. Thereafter the xerogel is allowed to cool to ambient temperature or cooling is accelerated by circulation of a cool dry inert gas such as nitrogen through the gel. Ethylene is also satisfactory as a cooling gas. After the gel has been cooled, the reactor is depressurized to atmospheric pressure or below.

Alternatively, the silica xerogel can be charged into a pressure vessel which is then pressurized with an inert gas. The xerogel is then heated while water in the vapor state only is allowed to admix with the inert gas which surrounds the gel. The inert gas is kept saturated with water vapor. This may be accomplished, for example, by initially charging liquid water into the vessel while keeping it separate and out of contact with the xerogel. The reactor is then closed, pressurized and heated externally. In this case, the liquid water is also heated and caused to vaporize, saturating the gas blanket with water vapor at all temperatures. The amount of water can be limited so as to be fully vaporized at treatment temperature. At the end of the treatment, the vessel is depressurized at the treatment temperature, and swept with cool, moist inert gas to cool to ambient temperature without dehydration of the xerogel yet not allowing liquid water condensation on the gel.

The resulting xerogel is characterized by:

| | |
|---|---|
| Martin diameter: | 0.5–25.0 mm, preferably 2.0–5.0 mm |
| Bulk density: | 0.35–0.75 g/cc, preferably 0.42–0.70 g/cc |
| Pore volume: | 0.40–2.2 ml/g, preferably 0.44–1.15 ml/g |
| BET surface area: | 20–800 m$^2$/g |
| Average crush strength (dry) of 50 particles: | >4 pounds |
| Mechanically stable to aqueous solutions and steam to 350°C. | |

After the steam treatment, the xerogel is impregnated with the active catalytic material. The xerogel is suitable for supporting a whole spectrum of solid catalysts involving especially elements of Groups I B, II B, IV B, V, VI B, VII B, and VIII of the Periodic Table of the elements appearing at pages 60–61 of Lange's Handbook of Chemistry (Revised 10th Ed.), and more especially the following elements, their salts, their oxides, their acids, their alloys, their heteropolyacids or salts, or any mixtures thereof: Cu, Ag, Au, Zn, Cd, Hg, Ti, Bi, Sb, Zr, Hf, V, Nb, Ta, Cr, Mo, W, Mn, Re, N, P, As, Fe, Co, Ni, Ru, Os, Ir, Rh, Pd, and Pt, with the optional additional impregnation of the support with phosphoric acid solution or $I_2$.

These catalysts are useful in a very large number of fixed bed, vapor or mixed gas liquid trickle bed catalytically promoted industrially important reactions including, for example, (1) the oxidation of ethylene to acetic acid, (2) the oxidation of ethylene in the presence of acetic acid to vinyl acetate, (3) the oxidation of propylene in the presence of water to acrylic acid, (4) the oxidation of xylenes to the corresponding aromatic acids, e.g., phthalic, isophthalic, or terephthalic acids, (5) the ammonia oxidation of propene to acrylonitrile, (6) the oxidative dehydrogenation of n-butylene, (7) the reductive amination of nitriles, (8) the oxidation of exhaust gas from internal combustion engines, (9) the hydrogenation of unsaturated compounds, (10) olefin polymerization, (11) oxidation of paraffin hydrocarbons, (12) oxidation of $SO_2$ to $SO_3$, (13) the hydrogenation of phenol to cyclohexanol, (14) oxosynthesis, (15) hydrogenation of nitroso compounds, and (16) the oxidation of ethanol to acetic acid.

The present invention thus opens up the possibility of using regular density or intermediate density silica xerogel granules or extrusions as supports for heretofore non-feasible fixed bed heterogeneous oxidation catalyst compositions which require the use of aqueous and/or alkaline medium in their preparation. As an example, very active oxidation catalysts are prepared by impregnating a support with an aqueous solution of sodium chloropalladite ($Na_2PdCl_4$) and chloroauric acid ($HAuCl_4$), concentrating that mixture on a support by heat until the granules are free flowing (dry), then immersing the granules in an alkaline formaldehyde solution to reduce the salts to the metals, Pd and Au. The granules are then drained and washed with water containing a trace of acetic acid to wash out chloride ion which is poisonous to oxidation reactions and also to wash out sodium chloride, sodium hydroxide and other impurities. The resulting preparation, when impregnated with aqueous $H_3PO_4$ is catalytically active in the oxidation of ethylene to acetic acid. However, non-steam treated regular density xerogel disintegrates in the presence of aqueous solutions and thus can neither be impregnated from nor washed with aqueous solutions. Furthermore, it becomes gelatinous in the presence of alkaline solutions.

The presence of alkali has been found to be very beneficial in the reduction of the palladium salt with several possible reducing agents such as sodium borohydride, hydrogen, hydrazine, hydroxylamine, CO, $NH_3$ or alcohols. However, alkaline solutions cause decrepitation of nonsteamed intermediate density gels and causes them to become gelatinous and completely unsuitable as fixed bed catalyst supports. Extrusions made from powdered intermediate density silica gels are also greatly weakened when exposed to alkaline solutions.

Pre-treatment of the regular density of the intermediate density granules and extrusions with steam at elevated temperatures and pressures causes them to become mechanically stable to aqueous solutions and to alkaline solutions and thus suitable for supports in preparing the aforementioned catalysts. There is thus made available catalysts on silica gel supports which are characterized by high specific pore volumes such as the intermediate density silica xerogels or high specific surface areas such as the regular density silica xerogels. There is an added advantage from the steam treatment of an adequate crush strength for the finished catalysts.

A variety of methods can be used for the deposition depending on the finished catalyst desired. In one method suitable for the deposition of metals, mixtures of metals and alloys of metals such as noble metals, oxides and salts of metals or mixtures of oxides or metals with oxides, a soluble precursor or mixed precursor of the catalytic materials are dissolved in an appropriate volatile solvent and the steam treated silica xerogel impregnated with the resulting solution, drained and then the solvent evaporated until the gel is in a state of near dryness. The precursors are then converted to the final catalytic material by the following treatments singularly or in combination: drying, reduction, hydrogenation, oxidation, alkali or acid treatment, or thermal decomposition. The gel may then be washed with a suitable solvent, if required, to remove undesirable ions or soluble extraneous material and then dried under relatively mild conditions. The gel can also then be impregnated, if desired or required, with phosphoric acid or other catalytic liquid and dried to produce the final catalyst.

In some instances, it may be advantageous to pretreat the steam treated xerogel with an alkaline or acid solution prior to catalyst deposition.

In another method, solutions of the catalytic materials or their precursors may be sprayed into the steam treated silica gel particles as they are being tumbled and dried in a rotating vessel.

The steaming process, catalyst impregnation process, and catalytic reaction can be performed in the same reactor or in separate reactors as desired.

Electron micrographs of silica gel show that the physical structure can be described as a coherent aggregate of elementary particles of roughly spherical shape having a diameter of the order of 100 A. The elementary particle is an irregular three dimensional network of $SiO_4$ tetrahedra, each silicon atom being linked to four oxygens and each oxygen being linked to two silicons. At certain sites, the elementary particles may be linked together by Si-O-Si bridges. The particle surface is covered with hydroxyl groups which are responsible for the hydrophilic nature of normal silica gel.

The steaming process involves a vapor phase transport of matter resulting in the growth of large elementary particles at the expense of small ones, and resulting in the enlargement of the pores and loss in surface area. The transport of solid material during steaming results in the formation of fillets between the particles by deposition of the material in the regions of contact. Undoubtedly, this contributes to the enhanced crush strength of the gel. The transport of material from a small elementary particle to a larger one is of molecular character. The silica gel skeleton is not affected during this process and, therefore, the pore volume does not change.

The change also results in the increased resistance to crushing of the dry xerogel granule and of the xerogel granule impregnated with the active catalyst.

It will be recognized that the discussion above relates to the theory behind the invention. It has been set forth to assist in understanding the nature of this invention but I do not wish to be limited thereby.

With respect to xerogel granules, the effect of the steam treatment of the instant invention on mechanically strengthening regular density xerogel is even more marked than for the intermediate density xerogel. The intermediate density xerogels become gelatinous but do not shatter or disintegrate on immersion in aqueous solution or alkaline solutions, while non-steamed regular density silica xerogel granules do so shatter or disintegrate.

The following Examples are set forth to further illustrate the invention but are not intended to limit it. Unless otherwise specified, all parts and percentages are by weight and all temperatures are in degrees centigrade unless otherwise specified.

EXAMPLE 1

A sample of intermediate density silica xerogel granules having particles retained on 6 mesh screen (U.S. Standard Sieve Series) and manufactured by the Davison Chemical Co. having the following properties:

| Grade | 57 ID gel |
|---|---|
| Average crush strength (lbs) | 2.5 |

-continued

| | |
|---|---|
| Pore volume (cc/g) | 1.04 |
| Surface area (m²/g) | 350 |
| Average pore diameter (A) | 120 |
| Total volatile (wt.%-ca 955° C) | 4.5 |
| Bulk density (lbs/ft³) | 27 |
| $SiO_2$ (wt.%-dry basis) | 99.5 |
| Fe (wt.%-dry basis) | 0.02 |
| $Na_2O$ (wt.%-dry basis) | 0.09 | was placed in a glass liner which was then inserted in a 250 ml stainless steel autoclave. 9 ml of liquid water were placed in the bottom of the autoclave but outside the liner. The autoclave was then closed and electrically heated externally with a heating jacket to 270° C. and held at that temperature under the autogeneous steam pressure developed for 64 hours. The autoclave was then cooled to room temperature, opened, and the steam treated gel removed. The average crush strength had increased to 6.5 lbs.

The treated xerogel was coated with palladium and gold metals to give approximately 1% Pd and about 0.5% Au by impregnating the xerogel with a solution of a palladium salt and chloroauric acid, followed by reduction to the metals with an aqueous, alkaline solution of formaldehyde.

5 g of the catalyst thus prepared were placed in one arm of a 6 long × ½ inch inner diameter glass tube and rested on a plug of glasswool on the bottom. The tube was immersed in an oil bath at 140° C. and subjected to a flow of oxygen containing 15% ethylene and saturated with glacial acetic acid at 75° C. (by bubbling the gas through glacial acetic acid) using a flow rate of 2 liters per hour and a pressure of 10 psig. The exit gas was passed through a cold trap at about −70° C. to condense the liquid.

Analysis showed the production rate of vinyl acetate from the 5 g of catalyst for the first 5 days to be 7.3, 7.5, 7.6, 7.5 and 7.3 mmol/hr, respectively.

EXAMPLE 2 (Comparison)

An attempt was made to repeat the preparation of the catalyst in Example 1 by depositing the metals on the same silica gel without the steaming treatment. The gel disintegrated into a soft, plastic, gelatinous mass after contacting with the aqueous alkaline solution containing formaldehyde.

EXAMPLE 3

150 ml of cylindrically shaped extrusions of grade 57 ID xerogel fines measuring ⅛ inch diameter and from ⅛ inch to about ¾ inch long, (SMR 7-3741; Davison Chemical Co.), 300 m²/g surface area, were placed in a glass liner which were then inserted into a 250 ml stainless steel autoclave. 10 ml of liquid water was placed in the autoclave outside the liner. The autoclave was closed and heated electrically to 280° C. for 16 hours under the autogeneous steam pressure developed after which the autoclave was cooled and opened. The steamed extrusions were then coated with palladium and gold as described in Example 1. The resulting catalyst was employed to oxidize ethylene in the presence of acetic acid and oxygen to vinyl acetate by the procedure described in Example 1. The production rate of 5 g of catalyst for the first 5 days was 8.25, 8.46, 8.45, 8.49 and 8.24 mmol/hr of vinyl acetate, respectively.

EXAMPLE 4 (Comparison)

An attempt was made to repeat the preparation of the catalyst of Example 3 using the same xerogel extrusions without the steam treatment. A gelatinous mass resulted when the alkaline reducing reagent was used and the material was unsuitable for fixed bed catalytic use.

EXAMPLE 5

The catalyst prepared in Example 1 was converted into a catalyst for oxidizing ethylene to acetic acid by impregnating it with a phosphoric acid solution prepared from 4.16 parts of 85% $H_3PO_4$ and 13.6 parts deionized water, followed by drying until the granules tumbled freely as the catalyst was tumbled in an open, slowly rotating, glass dish under a flow of hot air generated by a heat gun. The $H_3PO_4$ impregnated catalyst was placed in a reactor through which was passed a gas mixture of ethylene, oxygen and water vapor in a volume ratio of 5:1:4, respectively, at 150° C. and 50 psi and an hourly vapor space velocity of 298 volumes reactant gas to 1 volume catalyst. The ethylene and oxygen were catalytically converted to acetic acid and acetaldehyde; 75% of the oxygen was converted to acetic acid with a selectivity of 56% and to acetaldehyde with a selectivity of 6% and to $CO_2$ with a selectivity of about 23%; each of the selectivities being based on the total ethylene reacted.

EXAMPLE 6

A sample of regular density xerogel granules (grade 03 RD gel - Davison Chemical Co.), retained on an 8 mesh screen, and having the following properties:

| | |
|---|---|
| Average crush strength | 8.2 lbs |
| BET surface area (m²/g) | 800 |
| Pore volume (cc/g) | 0.45 |
| Average pore diameter (A) | 22 |
| Total volatile (wt.%-ca 955° C) | 6.0 |
| Bulk density (g/cc) | 0.69 |
| Composition (wt.%-dry basis) | |
| $SiO_2$ | 99.7 |
| Fe | 0.03 |
| $Na_2O$ | 0.02 | was placed in a glass liner which was then inserted into a 250 ml stainless steel autoclave. 10 ml of liquid water were placed in the bottom of the autoclave but outside the liner. The autoclave was closed and externally heated electrically to 270° C. and held at that temperature under the autogeneous steam pressure developed for 16 hours. The autoclave was then cooled to room temperature, opened and the steam treated xerogel removed. The average crush strength had increased to 12.6 lbs.

The steam treated RD xerogel was then coated with Pd and Au as described in Example 1.

EXAMPLE 7 (Comparison)

An attempt was made to repeat the preparation of the catalyst of Example 6 using the same regular density xerogel granules but without the steam treatment. The attempt failed because the gel disintegrated when it was immersed in the coating solution and then changed to a soft, gelatinous mass when contacted with the aqueous alkaline solution containing formaldehyde.

EXAMPLE 8

60.72 g of extruded ⅛ inch diameter and about ¾ inch long ID silica xerogel having a specific surface area of 300 m²/g and a pore volume of 0.45 cc/g (SMR 7-3741; Davison Chemical Co.) was placed in a glass liner which was then placed in a 250 ml Magna-Dash stainless steel autoclave. 10 ml of liquid water was placed in the autoclave outside the liner and the autoclave was closed. The reactor was then heated to 280° C. and held there under the autogeneous steam pressure developed for 17 hours, after which the autoclave was cooled to ambient temperature, the extrudate removed and vacuum dried at 100° C. for 2.5 hours. The final weight of the xerogel extrudate was 58.21 g.

A catalyst was prepared containing 1% Pd and 0.5% Au using an aqueous alkaline formaldehyde solution to reduce the palladium and gold to the metals. 30 ml of the catalyst were treated with 20 ml of a solution prepared by diluting 2.57 g of 85% $H_3PO_4$ to 20 ml, and then dried on a rotating glass dish under a stream of hot air to produce the final catalyst.

The 30 ml of final catalyst was placed in a reactor and used to catalytically oxidize propylene to acrylic acid at 195° C. at atmospheric pressure using a mixed gas composed of propylene at a feed rate of 10 cc/min, air at a feed rate of 178 cc/min and water vapor at a feed rate of 160 cc/min, the latter being achieved by passing the air and propylene mixture through water at 80° C. After a run of 28 hours, acrylic acid was produced at a rate of 24.8 mmol/liter catalyst/hour.

EXAMPLE 9 (Comparison)

An attempt was made to prepare the catalyst of Example 8 from the same silica xerogel extrudate within a steam treatment. The attempt failed because the treatment with the aqueous alkaline formaldehyde reducing agent caused the extrudate to change into a soft, gelatinous mass which was unsuitable as a fixed bed catalyst.

EXAMPLE 10

A sample of regular density xerogel silica gel granules (grade 03 RD gel - Davison Chemical Co.), retained on an 8 mesh screen, and having the following properties:

| | |
|---|---|
| Average crush strength (lbs) | 8.2 |
| Pore volume (cc/g) | .45 |
| Surface area (m²/g) | 800 |
| Average pore diameter (A) | 22 |
| Total volatile (wt.%-ca 955° C) | 6.0 |
| Bulk density (lbs/ft³) | 43 |
| $SiO_2$ (wt.%-dry basis) | 99.7 |
| Fe (wt.%-dry basis) | 0.03 |
| $Na_2O$ (wt.%-dry basis) | 0.03 | was placed in a glass liner which was then inserted into a 250 ml stainless steel autoclave. 10 ml of liquid water were placed in the bottom of the autoclave but outside the liner. The autoclave was closed and externally heated electrically to 270° C. and held at that temperature under the autogeneous steam pressure developed for 16 hours. The autoclave was then cooled to room temperature, opened and the steam treated xerogel removed. The average crush strength had increased to 12.6 lbs.

The steam treated regular density xerogel was then coated with Pd.

The catalyst is used in the continuous mixed liquid-gas phase trickle bed catalytic hydrogenation of N-nitrosodimethylamine (NDMA) to unsymmetrical dimethylhydrazine (UDMH) as follows.

200 ml (140.5 g) of the catalyst are charged to a jacketed stainless steel reactor which is then closed. Oil at 26° C. is circulated through the jacket to keep the bed at that temperature. The reactor is flushed with nitrogen, then hydrogen, then pressured to 60 psig with hydrogen.

The feed entering into the reactor above the bed consists of hydrogen gas and an anaerobic solution of 20% N-nitrosodimethylamine in oxygen-free water. The latter is fed into the reactor at a rate of about 60 gal/ft³ catalyst/hour.

Pressure is maintained at 60 psi by hydrogen under higher pressure entering through a valve controlled by a pressure transmitter located at a port at the top of the reactor above the bed and an associated controller. It is thus fed at the rate it is consumed.

Liquid product is removed through a valve located below the bed and controlled by a differential pressure cell and associated controller so as to maintain a liquid level at a point below the catalyst bed.

Under steady state conditions, a substantial proportion of the N-nitrosodimethylamine is hydrogenated to unsymmetrical dimethylhydrazine.

EXAMPLE 11

A vertically mounted jacketed stainless steel reactor is charged with 200 ml (140.5 g) of a catalyst prepared from regular density xerogel silica gel granules as in Example 10, closed, then hot oil is circulated through the jacket to heat the catalyst bed to and maintain it at 125° C.

A preheated (125° C.) pressurized gaseous mixture comprised of 64.1 parts by weight nitrogen, 19.5 parts by weight oxygen and 16.4 parts by weight ethanol is pumped continuously into the top of the reactor from where it passes through the catalyst bed at 75 psi pressure, and during which the ethanol is continuously catalytically oxidized in vapor phase to acetic acid, acetaldehyde and $CO_2$. The reacted gas mixture passes out of the bottom of the reactor through a valve where pressure is let down to atmospheric. That valve is controlled with a pressure transmitter (connected to a port at the top of the reactor above the bed) together with a controller to maintain reaction pressure at 75 psi. Acetic acid and acetaldehyde are condensed to liquid state by cooling the effluent gas stream to 0° C. in a condenser.

Feed rates in mmol/hr of nitrogen, oxygen and ethanol are 591, 157 and 92, respectively, and product rates in mmol/hr for acetic acid, acetaldehyde and $CO_2$ are 71, 2.7 and 36.5, respectively.

Various changes and modifications can be made in the process and products of this invention without departing from the spirit and the scope thereof. For example, the catalysts of this invention can also be used in a moving bed. The various embodiments disclosed herein were for the purpose of further illustrating the invention but were not intended to limit it.

I claim:

1. In a catalyst comprising an active catalytic material and a preformed support, wherein the active catalytic material is a metal, salt, oxide, acid, alloy, or heteropolyacid of an element of Groups I B, II B, IV B, V, VI B, VII B and VIII of the Periodic Table of Elements and mixtures thereof, the improvement which comprises employing as the support a regular or intermediate density silica xerogel which has been steam treated at a temperature up to 300° C.

2. The catalyst of claim 1 wherein said xerogel has a Martin diameter of 0.5–25.0 mm, a bulk density of 0.35–0.75 g/cc, a pore volume of 0.4–2.2 ml/g, a BET surface area in the range of 20-800 m²/g, an average crush strength of 50 particles being not less than 4 pounds and having the following chemical composition in terms of weight percent dry basis: $SiO_2$ over 99%; $Fe_2O_3$ 0.01–0.03%; $Na_2O$ 0.02–0.09%; and $Al_2O_3$ less than 0.4%.

3. The catalyst of claim 2 wherein the Martin diameter is 2.0–5.0 mm, the bulk density is 0.42–0.70 g/cc, and the pore volume is 0.44–1.15 ml/g.

4. In a catalyst comprising an active catalytic material and a pre-formed support, wherein said active catalytic material is palladium, the improvement which comprises employing as the support a regular or intermediate density silica xerogel which has been steam treated at a temperature up to 300° C.

5. The catalyst of claim 4 wherein said active catalytic material additionally contains $H_3PO_4$.

6. A process for the preparation of the catalyst of claim 1 comprising steam treating an intermediate density or regular density silica xerogel at a temperature of 149° to 300° C., impregnating the resulting steam treated xerogel with a precursor of said active catalytic material and converting said active catalyst precursor to said active catalytic material.

7. The process of claim 6 wherein said xerogel is in the form of granules.

8. The process of claim 6 wherein the xerogel is in the form of extrudates.

9. The process of claim 6 wherein the impregnation of said precursor is effected from an aqueous or alkaline solution of said precursor.

10. The process of claim 6 wherein said precursor is converted to said active catalytic material in an alkaline medium.

11. The process of claim 6 wherein said intermediate density or regular density silica xerogel which is steam treated has a Martin diameter of 0.5–25.0 mm, a bulk density of 0.35–0.75 g/cc, a pore volume of 0.4–2.2 ml/g, a BET surface area in the range of 20–900 m²/g, an average crush strength of 50 particles being not less than 2.0 pounds and having the following chemical composition in terms of weight percent dry basis: $SiO_2$ over 99%; $Fe_2O_3$ 0.01–0.03%; $Na_2O$ 0.02–0.09%; and $Al_2O_3$ less than 0.4%.

12. The process of claim 11 wherein the Martin diameter is 2.0–5.0 mm, the bulk density is 0.42–0.70 g/cc, and the pore volume is 0.44–1.15 ml/g.

13. The process of claim 11 wherein said xerogel is an intermediate density xerogel having a bulk density of 0.35–0.48 g/cc, a pore volume of 0.80–2.2 ml/g, and a BET surface area of 200–500 m²/g.

14. The process of claim 11 wherein said xerogel is a regular density xerogel having a bulk density of 0.65–0.75 g/cc, a pore volume of 0.3–0.5 ml/g, and a BET surface area of 600–900 m²/g.

15. The catalyst of claim 4 wherein said active catalytic material additionally contains gold metal.

16. The catalyst of claim 4 wherein said active catalytic material additionally contains $I_2$.

17. A process for the preparation of a supported catalyst comprising steam treating an intermediate density or regular density silica xerogel at a temperature of 149°–300° C., impregnating the resulting steam treated xerogel with an aqueous solution of a palladium salt, and converting the palladium salt to palladium metal by contact with an alkaline solution of a reducing agent.

18. The process of claim 17 wherein said salt is $Na_2PdCl_4$ and said reducing agent is formaldehyde.

* * * * *